US007740825B2

(12) United States Patent
Tohji et al.

(10) Patent No.: US 7,740,825 B2
(45) Date of Patent: Jun. 22, 2010

(54) METHOD FOR FORMING A CARBON NANOTUBE AGGREGATE

(75) Inventors: Kazuyuki Tohji, Miyagi (JP); Yoshinori Satoh, Miyagi (JP); Hirohisa Kikuyama, Osaka (JP); Masahide Waki, Osaka (JP); Shinji Hashiguchi, Osaka (JP); Yasutaka Tashiro, Osaka (JP)

(73) Assignee: Stella Chemifa Corporation, Osaka (JP)

( * ) Notice: Subject to any disclaimer, the term of this patent is extended or adjusted under 35 U.S.C. 154(b) by 741 days.

(21) Appl. No.: 11/547,199

(22) PCT Filed: Mar. 31, 2005

(86) PCT No.: PCT/JP2005/006359

§ 371 (c)(1),
(2), (4) Date: Feb. 28, 2007

(87) PCT Pub. No.: WO2005/095274

PCT Pub. Date: Oct. 13, 2005

(65) Prior Publication Data

US 2007/0209093 A1    Sep. 6, 2007

(30) Foreign Application Priority Data

Mar. 31, 2004    (JP) .............. 2004-106143

(51) Int. Cl.
*D01F 9/12*    (2006.01)
(52) U.S. Cl. .................... 423/447.1; 423/491
(58) Field of Classification Search ............... 423/439, 423/447.1, 447.6, 449.4, 491
See application file for complete search history.

(56) References Cited

U.S. PATENT DOCUMENTS 6,645,455 B2 *  11/2003  Margrave et al. ......... 423/447.1

FOREIGN PATENT DOCUMENTS

JP    2003-63814    3/2003
JP    2003-306320    10/2003

* cited by examiner

*Primary Examiner*—Edward M Johnson
(74) *Attorney, Agent, or Firm*—Young & Thompson

(57) ABSTRACT

A carbon nanotube aggregate and a method for forming a carbon nanotube aggregate are provided. The carbon nanotube aggregate can be formed by treating carbon nanotubes with fluorine gas and sintering the resulting fluorinated carbon nanotubes. A carbon nanotube aggregate can be formed which does not contain a binder or resin matrix.

15 Claims, 7 Drawing Sheets

METHOD FOR FORMING A CARBON NANOTUBE AGGREGATE

TECHNICAL FIELD

The present invention relates to an aggregate of carbon nanotubes in which the carbon nanotubes alone can constitute the aggregate, and which is practically applied for various fields such as thermal conductive materials and high strength materials as well as electronic materials and nanotechnology materials by taking advantage of its geometric and physicochemical characteristics.

BACKGROUND ART

In recent years, the nanotechnology has been highlighted and the carbon nanotube has attracted the attention of various fields. Development of practical application to probes, micromachines, conductive materials, thermal conductive materials, fuel batteries and solar batteries or many interesting uses for hydrogen storage materials has been actively-studied by taking advantage of specific functions of the carbon nanotubes. Conventionally, formed articles of carbon materials are accomplished by using resins, rubbers, thermoplastic elastomers, adhesives, paints, inks, metals, alloys, ceramics, cements, gelled materials, paper, fabrics, nonwoven fabrics and the like as a matrix. The matrix has been selected depending on required performances such as hardness, mechanical strength, heat resistance, electric properties, durability and reliability of an objective complex formed article. Publications for forming the complex using the carbon nanotubes include the following references, and the technologies to combine the carbon nanotube in place of conventional carbon black and carbon fibers with the resin are disclosed.

Patent Document 1: JP 2002-273741-A Publication
Patent Document 2: JP 2003-221510-A Publication
Patent Document 3: JP 2003-12939-A Publication
Patent Document 4: JP 2002-265209-A Publication In Patent Document 1, a carbon nanotube complex formed article formed in a state in which the carbon nanotubes are arranged in a constant direction in the matrix has been described. At least one organic polymer selected from thermoplastic resins, curable resins, rubbers and thermoplastic elastomers is used as the matrix.

In Patent Document 2, a thermoplastic resin composition composed of (A) 20 to 99.95% by mass of a thermoplastic resin and (B) 0.05 to 20% by mass of carbon nanotubes comprising (C) 0.05 to 30 parts by mass of a flame retardant and 0 to 2 parts by mass of a polyfluoroolefin resin relative to 100 parts by mass of a total amount of (A) and (B) is disclosed as a conductive thermoplastic resin composition wherein an appearance of a molded article is good, mechanical strength is enhanced and flame resistance is high.

In Patent Document 3, a carbon-containing resin composition wherein components [A] substantially do not form an aggregate one another and are uniformly dispersed in components [B] without interlacing and the component [A] is in the range of 0.01 to 1.8% by weight and the component [C] is in the range of 0.1 to 55% by weight relative to 100% by weight of the composition is disclosed as the carbon-containing resin composition having excellent dynamic property and moldability and if necessary combining with excellent conductivity.

Component [A]: Carbon nanotubes with an average diameter of 1 to 45 nm and an average aspect ratio of 5 or more
Component [B]: Resin
Component [C]: Filler These prior arts all relate to enhancing electric, thermal or mechanical nature by adding the carbon nanotube to the matrix. The addition of the carbon nanotube adamantly aims at enhancing the physical property of the matrix, and does not enable to use the excellent physical property of the carbon nanotube in a macro state. The present inventors have thought up that it is the most desirable to construct an aggregate composed of the pure carbon nanotubes alone in order to maximally leverage the physical property of the carbon nanotube. Thus, it has been made a problem to obtain the aggregate of the carbon nanotubes, which was not carried out in the above prior publications.

DISCLOSURE OF INVENTION

Problem to be Solved by the Invention

In the above prior arts, no aggregate of the carbon nanotubes alone in which the property of the carbon nanotubes has been kept can be provided, and the presence of the matrix is essential. A composite using a resin, a rubber or a thermoplastic elastomer as the matrix uses a plasticizer in a large amount for enhancing the dispersion of the carbon nanotubes, and thus, a viscosity of the resin is necessary to be reduced. There is also a method of directly adding the carbon nanotubes, but in this case, there is a shortcoming in that the resin itself can be deteriorated upon kneading. Furthermore, in the composite obtained by such a formation, the mechanical strength is not enhanced due to unevenness of the composition in the matrix after the formation in some cases, and no compatibility is obtained due to effects of the plasticizer and resin components when used as biomaterials in some cases. These cases are problematic.

It is an object of the present invention to provide a carbon nanotube aggregate without using a matrix such as a resin, and a method for producing the same.

Means for Solving Problem

The present invention is a carbon nanotube aggregate characterized by treating characterized in that carbon nanotubes are treated with 0.1 to 100% fluorine gas ($F_2$) in a fluorine based resin container and sintering the resulting fluorinated carbon nanotubes in a non-oxidizing atmosphere under an environment at 250 to 3000° C. and at 10 to 600 MPa, and a method for producing the same. The present inventors has found that it is possible to form the carbon nanotube aggregate which does not contain the resin and other binder at all.

The carbon nanotube aggregate of the present invention is characterized by being formed as a structure of the carbon nanotubes alone which does not contain the resin and other binder as the matrix. The biocompatible material of the present invention is characterized by being composed of the above aggregate. Artificial joint materials, dental materials and artificial bone materials are preferable as biocompatible materials. The electric electronic material of the present invention is characterized by being composed of the above aggregate. Biological electrode materials, battery electrode materials, fuel battery electrode materials and electric bilayer capacitor electrode materials are preferable as the electric electronic materials.

Effect of the Invention

As described above, the present invention is composed of a step of fluorinating and a step of sintering fluorinated multiple carbon nanotubes, and enables to form the aggregate of carbon nanotubes alone. The carbon nanotube aggregate is composed of the carbon nanotubes alone, and has possibility for various fields because of being constructed as those combining its properties.

BEST MODES FOR CARRYING OUT THE INVENTION

Figure 1:
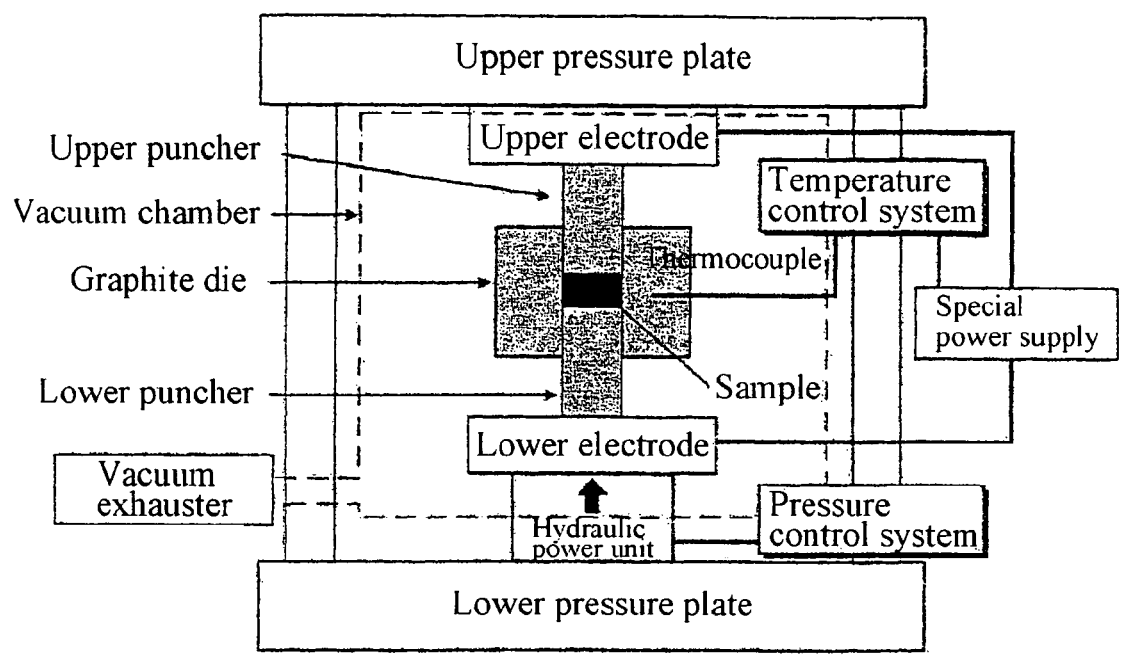
FIG. 1 is a view showing an SPS sintering apparatus.

The present invention will be further described below based on embodiments.

In the present invention, multilayer carbon nanotubes synthesized by CVD method and supplied from Nano Lab (MA, USA) were used.

A type and a production method of the carbon nanotube used in the present invention are not particularly limited, and the carbon nanotube used in the present invention is formed by carbon, has a diameter of nanometer order and a large aspect ratio, and is filamentous. Methods for synthesizing the carbon nanotubes include an arc discharge method and a laser evaporation method in addition to a thermolytic CVD method and a plasma CVD method. The carbon nanotubes obtained by those methods can also be used.

In recent years, purification of the carbon nanotubes has been frequently reported, and by the use of the purer carbon nanotubes, it is possible to form the aggregate composed of their essence. Impurities include catalytic metals (e.g., Fe, Co, Ni), amorphous carbon and graphite particles upon producing the carbon nanotubes. When fluorinated and sintered as these metals are contained, no aggregate is formed in some cases. Carbon based impurities inhibit the fluorination and reduce the mechanical strength upon forming the aggregate in some cases.

In the present invention, the catalytic metal was removed by oxidation with air in atmosphere followed by treatment with hydrochloric acid. After the treatment, purification degrees of the catalyst and amorphous carbon were confirmed by observing using a field emission scanning electron microscope (SEM) (S-4100 supplied from Hitachi Ltd.) and a field emission transmission electron microscope (TEM) (HF-2000 supplied from Hitachi Ltd.). The purification method is not limited, and for example, the method described in Patent Document 4 can also be used.

In the present invention, the carbon nanotubes are fluorinated by reacting with fluorine ($F_2$) gas. A concentration of the fluorine gas is not particularly limited, but is preferably 1 to 100% and more preferably 1 to 50% in terms of handling the fluorine gas. An inert gas (He, Ar, $N_2$) could be used for dilution of the fluorine gas.

A temperature for the fluorination is not particularly limited, but is preferably 20 to 500° C. and more preferably 100 to 300° C. The reaction can be facilitated by treating at high temperature, but the treatment in a temperature environment in which covalently bound fluorine is desorbed reduces a yield and a treating efficiency. Meanwhile, the treatment at low temperature can make the treatment environment mild, but prolongs a treating time period and reduces the treating efficiency. Therefore, the temperature at 100 to 300° C. is more preferable. After the treatment, the degree of fluorine introduction was measured by change of weight and represented by [CFx=Number of fluorine atoms/Number of carbon atoms]. A C—F bond was identified by an infrared spectrometer (FTIR-8200PC supplied from Shimadzu Corporation) and an X-ray photoelectric spectrometer (AXIS-HSi supplied from KRATOS). Subsequently, it was identified by observation using SEM and TEM that no graphite due to degradation of the carbon nanotubes was produced.

In the present invention, it is preferable to remove the catalyst and the amorphous carbon used upon producing the carbon nanotubes wherever possible. When the catalyst is abundantly present, the catalyst is fluorinated and thus the efficiency to fluorinate the carbon nanotubes is reduced. It goes without saying that the amorphous carbon inhibits the efficiency of fluorination, and the amorphous carbon causes formation defect upon subsequent formation of the aggregate. Therefore, the purification of the carbon nanotubes is the step necessary for the fluorination and the formation of the aggregate.

The present invention also provides the method for preventing secondary contamination by treating the carbon nanotubes in the resin container without contacting with the metal in the step of fluorinating by fluorine ($F_2$) gas.

Generally in the step of fluorinating, a metallic pipe arrangement of SUS or nickel (Ni) is used, and the carbon nanotubes are directly placed therein and chemically modified with the fluorine ($F_2$) gas. In this method, members used for the pipe arrangement are contaminated. It is likely that this secondary contamination adversely affects the aggregate formation and the intended use of the aggregate. If the purified carbon nanotube is fluorinated in the fluorine resin, the secondary contamination can be prevented. For the fluorine based resin, polytetrafluoroethylene, tetrafluoroethylene-perfluoroalkyl vinyl ether copolymers, tetrafluoro-hexafluoropropylene copolymers, tetrafluoroethylene-ethylene copolymers, polychlorotrifluoroethylene, polyvinylidene fluoride, polyvinyl fluoride and the like could be used. It is preferable to use these resins for the reaction container because they are excellent particularly in heat resistance and are resistance to the fluorine ($F_2$) gas. Depending on the temperature at which the carbon nanotube is fluorinated, it is preferable particularly to use a perfluorinated resin in terms of heat resistant temperature of the resin.

Those resins enable to remove the contamination due to degraded components of the resin and adhered impurities, and further to make an inexpensive resin an alternative by previously being perfluorinated using fluorine ($F_2$) gas before fluorinating the carbon nanotube.

When the resin container is not used, the contamination can also be removed by washing with acid such as hydrofluoric acid and hydrochloric acid, but a fluorination degree can not be recorded, which is not preferable in terms of step management.

The fluorine ($F_2$) gas used in the present invention was generated from an electrolytic cell, stored in a steel bottle, and used. The concentration of hydrofluoric acid (HF) in the fluorine ($F_2$) gas was 50 ppm or less when analyzed by an infrared spectrometer (Infinity Gold HR supplied from Mattson).

The method for introducing a defect into the carbon nanotubes of the present invention is the treatment with nitric acid, but the defect may be introduced by other treatment.

It is preferable to use a spark-plasma sintering system (SPS system) (FIG. 1) in the step of sintering the carbon nanotubes one another to form the aggregates of the carbon nanotubes in the present invention.

Its principle is that a sintering temperature from low temperature to ultrahigh temperature of 2000° C. is freely set up to sinter by directly putting pulsed electric energy in spaces among green compact particles filled in a die punch mold made from graphite and effectively utilizing high energy of high temperature plasma generated in an instant and resistance heating of the sintered die.

In the present embodiment, the sintered die with an internal diameter Φ 20 mm and a height of 60 mm made from graphite was used, a raw material was filled therein and a disc-shaped solidification with a thickness of 2 mm and a diameter Φ 20 mm was made by controlling its mass. At that time, an operation procedure was (1) setting the sintered die filled with the raw material in an apparatus, (2) setting up the pressure, (3) deaerating inside a chamber and (4) heating.

The temperature for the formation method is not particularly limited, but is 250 to 3000° C., preferably 500 to 3000° C. and more preferably 500 to 2000° C. When the temperature is 250° C. or below, degassing upon the formation can not be efficiently performed, and when it is 500° C. or below, sufficient strength can not be given. By making the temperature within 2000° C., it is possible to inhibit thermolysis of the carbon nanotubes. The pressure is not particularly limited, but it is preferable to perform at 10 to 600 MPa, preferably 80 to 600 MPa and more preferably 80 to 120 MPa in terms of easy handling, efficiency upon the formation in the apparatus and the formed state of the aggregate. The formation method is not particularly limited, and it is possible to perform in the apparatus in which the atmosphere, the temperature and the pressure can be controlled. A treating time period is not particularly limited, but the treatment for 10 minutes, preferably 30 minutes and more preferably 60 minutes or more can efficiently degas upon the formation. The longer the time is, the more efficiently the degassing is performed, but there is an optimal time period of the degassing depending on the temperature and pressure condition.

A test piece is made from the resulting carbon nanotube aggregate, and the mechanical strength (flexural strength, Young's modulus) is measured by 3-point bending test (INSTRON 5582). The carbon nanotube aggregate is the same fragile material as other ceramic materials such as alumina, and a fine flaw on the sample surface is predicted to largely affect its strength. Thus, it is necessary to remove the flaw on the surface by polishing.

Biocompatibility was examined by implanting various samples in a pocket subcutaneously formed in an abdominal area in a Wistar strain male rat with 6 weeks of age.

In the carbon nanotube aggregate obtained according to the present invention, the aggregate composed of the carbon nanotubes alone can be provided because fluorine is desorbed upon the formation. Carbon is categorized into biologically inert species which is not chemically bound to bone tissue when categorized in terms of bioreactivity. Therefore, the carbon can be used as artificial joint materials, dental materials and artificial bone materials because of having the compatibility with biological tissues. Furthermore, by the use of having the compatibility, it is also possible to make the complex implanting an antibody or an antigen by chemically modifying the aggregate surface with another functional group.

The present invention will be described below with reference to representative examples of the invention. These are only exemplifications for illustration, and the present invention is not limited to the following examples.

Example 1

Purification of Carbon Nanotubes

Unpurified multilayer carbon nanotubes (100 mg) is fired and oxidized at 500° C. for 90 minutes in air. Subsequently, the oxidized sample (1 g) is placed in 6 M HCl (1 L) and left stand in an oven at 60° C. for 12 hours or more. Then, 500 mg of the filtrated and dried sample was placed in 2 M NaOH (500 mL) and refluxed for 6 hours. NaOH is removed by rinsing with hot water with filtrating. A filter residue was dried in the oven at 60° C. When confirmed using TEM, SEM and X ray photoelectron spectrometry, the filter residue was the purified multilayer carbon nanotubes from which amorphous carbon and the catalytic metal had been removed.

Example 2

Investigation of Fluorination Container

The carbon nanotubes (100 mg) purified in Example 1 are collected in each container (5 mL) of SUS316L, nickel (Ni), platinum (Pt) or polytetrafluoroethylene (PTFE), and the container is set in a chamber (30 mL) made from SUS316L to which electrolytic polish was given. Subsequently, vacuum replacement with nitrogen is performed in the chamber, and the temperature is raised to 250° C. at 2° C./minute under nitrogen flow (20 cc/minute) to perform a constant temperature treatment for 6 hours. After cooling, the vacuum replacement with 20% fluorine ($F_2$) gas diluted with nitrogen is performed, and 20% $F_2$ is run at 25 cc/minute. Then, the chamber was heated to the given temperature at 8° C./minute and the temperature was kept for 9 hours to flourinate. As a result, in the case of using the PTFE container, the good fluorination was performed without undergoing metallic contamination.

Table 1 shows the presence or absence of the metallic contamination and the fluorination degree, and it is found that the good fluorination without undergoing metallic contamination can be performed only in the PTFE container. The metallic contamination was identified using the X ray photoelectron spectrometer.

TABLE 1

| Container | Temperature at fluorination | Metal contamination | CFx | Remarks |
|---|---|---|---|---|
| SUS316L | 100 | No | 0.05 | |
| | 250 | Yes | 0.29 | |
| Ni | 100 | No | 0.08 | Colored |
| | 250 | Yes | 0.35 | |
| Pt | 100 | No | 0.09 | Mass of Pt |
| | 250 | Yes | 0.45 | was reduced |
| PTFE | 100 | No | 0.05 | |
| | 250 | No | 0.31 | |

$CF_x$ = Number of fluorine atoms/Number of carbon atoms = (Increased weight/19)/(Initial weight/12.01)

Example 3

Fluorinated Carbon Nanotubes

The multilayer carbon nanotubes (500 mg) purified in Example 1 are collected in the PTFE container (5 mL), and the container is set in the chamber (30 mL) made from SUS316L to which electrolytic polish was given. Subsequently, the vacuum replacement with nitrogen is performed in the chamber, and the temperature is raised to 250° C. at 2° C./minute under nitrogen flow (20 cc/minute) to perform the constant temperature treatment for 6 hours. After cooling, the vacuum replacement with 20% fluorine ($F_2$) gas diluted with nitrogen is performed, and 20% $F_2$ is run at 25 cc/minute. Then, the chamber was heated to 250° C. at 8° C./minute and the constant temperature treatment was performed for 9 hours.

The C—F bond in the treated multilayer carbon nanotubes was identified using the infrared spectrometer and the X ray photoelectron spectrometer. A peak in the vicinity of 1192.3 and a peak of C 1s289.5 eV (the charge was compensated by making unmodified carbon 285.0 eV) were identified in the infrared spectrometry (KBr pellet method) and the X ray photoelectron spectrometry, respectively. These peaks are attributed to the C—F bond.

Figure 2:
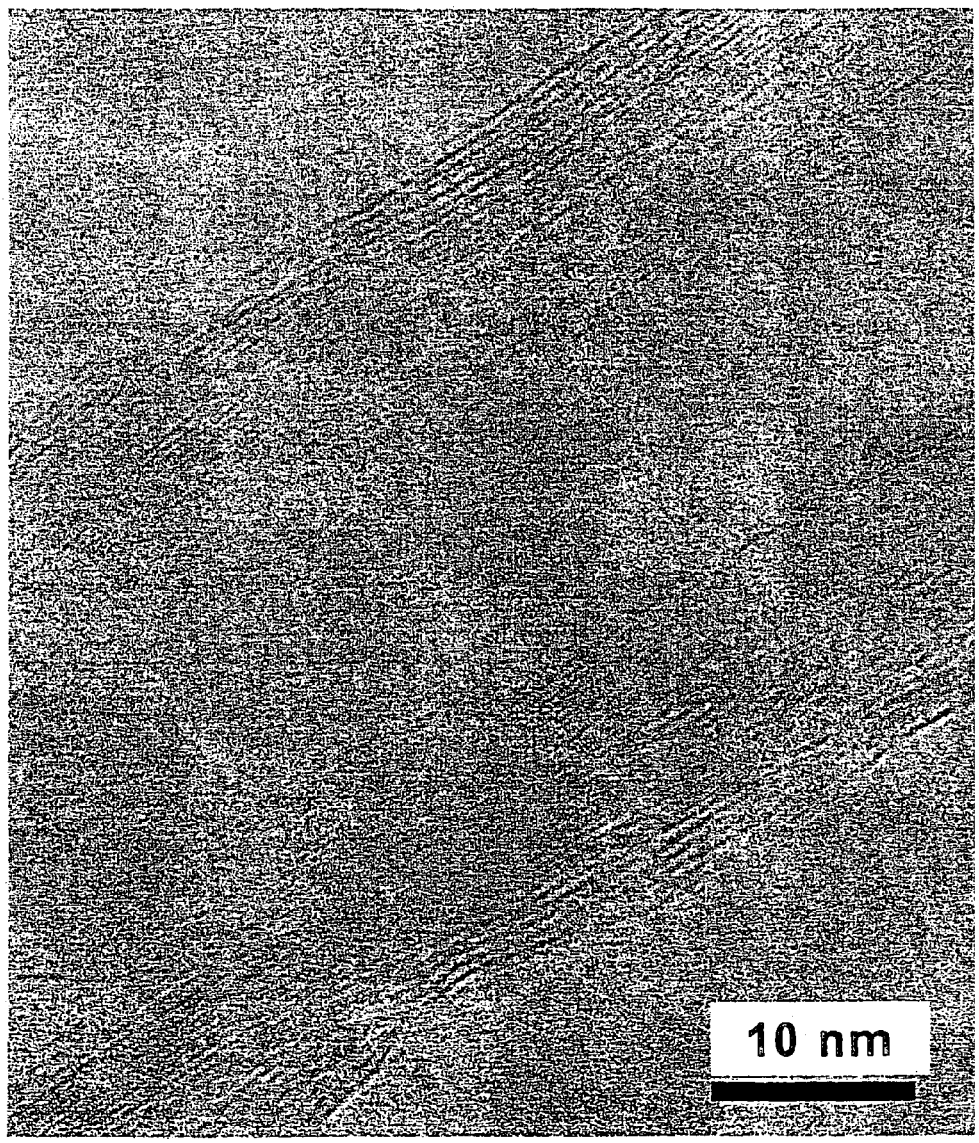
FIG. 2 is a TEM photograph of fluorinated carbon nanotubes.

A TEM photograph of the treated multilayer carbon nanotubes is shown in FIG. 2. From FIG. 2, it is identified that interlayer intervals of outer layers of the multilayer carbon nanotubes have become large, and it is found that fluorine has been introduced in the outer layers of the multilayer carbon nanotubes.

Furthermore, the observation by SEM and TEM was performed, and it was confirmed that graphite and the like due to the degradation of the carbon nanotubes were not generated.

$CF_x$ of the present fluorinated multilayer carbon nanotubes was 0.29.

Example 4

Production of Aggregate (1)

The fluorinated carbon nanotube obtained in Example 3 is dried in vacuum at 200° C. for 12 hours. This sample (1.3 g) is filled in the sintered die with an internal diameter Φ 20 mm and a height of 60 mm made from graphite. The sintered die is set in the SPS apparatus, compressed at 80 MPa and then deaeration inside the chamber is performed. The temperature was raised up to 500° C. at 25° C./minute and the constant temperature treatment was performed for 10 minutes. After cooling, a multilayer carbon nanotube aggregate was obtained. The resulting aggregate collapsed when being processed.

Example 5

Production of Aggregate (2)

The fluorinated carbon nanotube obtained in Example 3 is dried in vacuum at 200° C. for 12 hours. This sample (1.3 g) is filled in the sintered die with an internal diameter Φ 20 mm and a height of 60 mm made from graphite. The sintered die is set in the SPS apparatus, compressed at 80 MPa and then deaeration inside the chamber is performed. The temperature was raised up to 1000° C. at 25° C./minute and the constant temperature treatment was performed for 10 minutes. After cooling, a multilayer carbon nanotube aggregate was obtained. The resulting aggregate could be processed.

Example 6

Production of Aggregate (3)

The fluorinated carbon nanotube obtained in Example 3 is dried in vacuum at 200° C. for 12 hours. This sample (1.3 g) is filled in the sintered die with an internal diameter Φ 20 mm and a height of 60 mm made from graphite. The sintered die is set in the SPS apparatus, compressed at 120 MPa and then deaeration inside the chamber is performed. The temperature was raised up to 1000° C. at 25° C./minute and the constant temperature treatment was performed for 10 minutes. After cooling, a multilayer carbon nanotube aggregate was obtained. The resulting aggregate could be processed.

Example 7

Production of Aggregate (4)

The fluorinated carbon nanotube obtained in Example 3 is dried in vacuum at 200° C. for 12 hours. This sample (1.3 g) is filled in the sintered die with an internal diameter Φ 20 mm and a height of 60 mm made from graphite. The sintered die is set in the SPS apparatus, compressed at 120 MPa and then deaeration inside the chamber is performed. The temperature was raised up to 1000° C. at 25° C./minute and the constant temperature treatment was performed for 60 minutes. After cooling, a multilayer carbon nanotube aggregate was obtained. The resulting aggregate could be processed.

Example 8

Production of Aggregate (5)

The fluorinated carbon nanotube obtained in Example 3 is dried in vacuum at 200° C. for 12 hours. This sample (1.3 g) is filled in the sintered die with an internal diameter Φ 20 mm and a height of 60 mm made from graphite. The sintered die is set in the SPS apparatus, compressed at 200 MPa and then deaeration inside the chamber is performed. The temperature was raised up to 1000° C. at 25° C./minute and the constant temperature treatment was performed for 10 minutes. After cooling, parallel cracks occurred on a processed surface of a multilayer carbon nanotube aggregate.

Example 9

Introduction of Defect

The purified carbon nanotubes (500 mg) obtained in Example 1 is placed in 6 M $HNO_3$ (500 mL) and refluxed for 16 hours. Subsequently, a filter residue is washed with purified water until a filtrate becomes neutral with filtrating, and dried in the oven at 60° C. When the treated multilayer carbon nanotube was analyzed by the infrared spectrometry (KBr pellet method), the generation of carboxyl group was identified.

Figure 3:
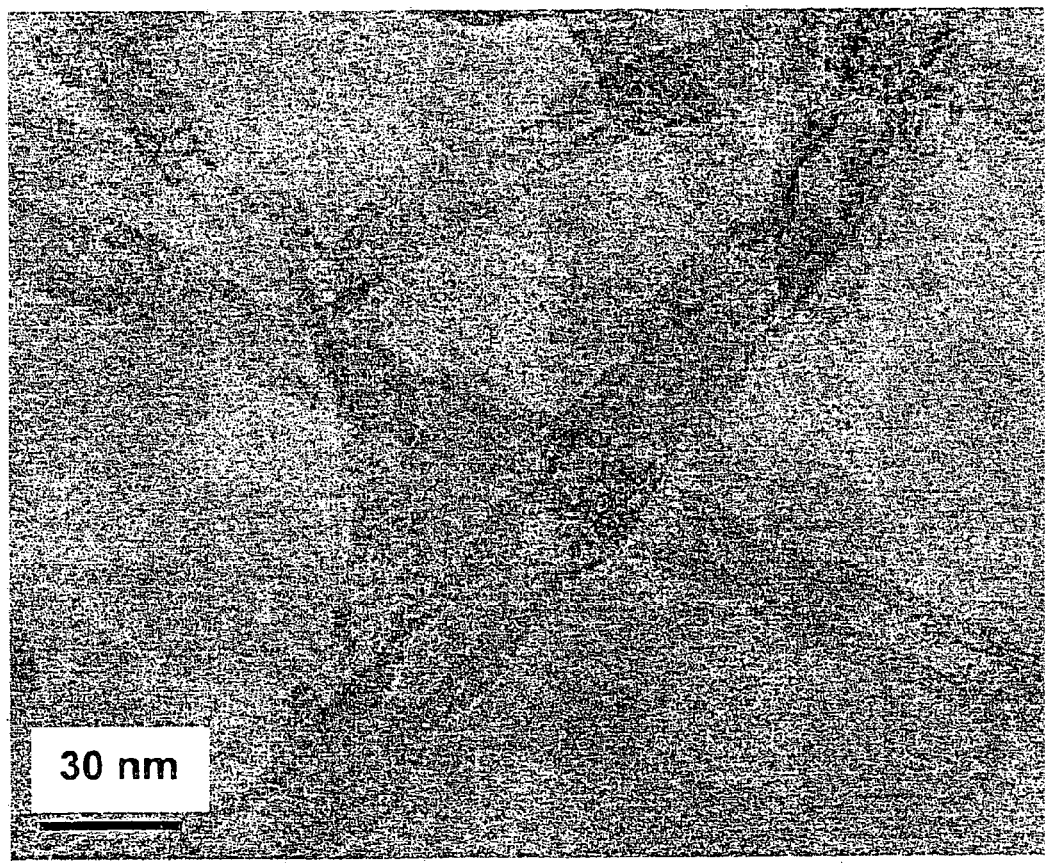
FIG. 3 is a TEM photograph of carbon nanotubes in which defects have been introduced.

A TEM photograph of the treated multilayer carbon nanotubes is shown in FIG. 3. From FIG. 3, it can be confirmed that the defect has been introduced in the outer layers of the multilayer carbon nanotubes.

Then, the multilayer carbon nanotubes (250 mg) in which the defect has been introduced are collected in the PTFE container (5 mL), and the container is set in the chamber (30 mL) made from SUS316L to which the electrolytic polish was given. Subsequently, the vacuum replacement with nitrogen is performed in the chamber, and the temperature is raised to 250° C. at 2° C./minute under nitrogen flow (20 cc/minute) to perform the constant temperature treatment for 6 hours. Subsequently, the vacuum replacement with 20% fluorine ($F_2$) gas diluted with nitrogen is performed, and 20% $F_2$ is run at 25 cc/minute. Then, the chamber was heated to 250° C. at 8° C./minute and the constant temperature treatment was performed for 9 hours.

$CF_x$ of this fluorinated multilayer carbon nanotubes in which the defect had been introduced was 0.31.

Example 10

Production of Aggregate (6)

The fluorinated multilayer carbon nanotube in which the defect was introduced obtained in Example 9 is dried in vacuum at 200° C. for 12 hours. This sample (1.3 g) is filled in the sintered die with an internal diameter Φ 20 mm and a height of 60 mm made from graphite. The sintered die is set in the SPS apparatus, compressed at 80 MPa and then deaeration inside the chamber is performed. The temperature was raised up to 1000° C. at 25° C./minute and the constant temperature treatment was performed for 10 minutes. After cooling, a defect multilayer carbon nanotube aggregate was obtained. The resulting aggregate could be processed.

Example 11

Production of Aggregate (7)

The fluorinated multilayer carbon nanotube in which the defect had been introduced obtained in Example 9 is dried in vacuum at 200° C. for 12 hours. This sample (1.3 g) is filled in the sintered die with an internal diameter Φ 20 mm and a height of 60 mm made from graphite. The sintered die is set in the SPS apparatus, compressed at 120 MPa and then deaeration inside the chamber is performed. The temperature was raised up to 1000° C. at 25° C./minute and the constant temperature treatment was performed for 10 minutes. After cooling, a multilayer carbon nanotube aggregate was obtained. The resulting aggregate could be processed.

Example 12

Figure 4:
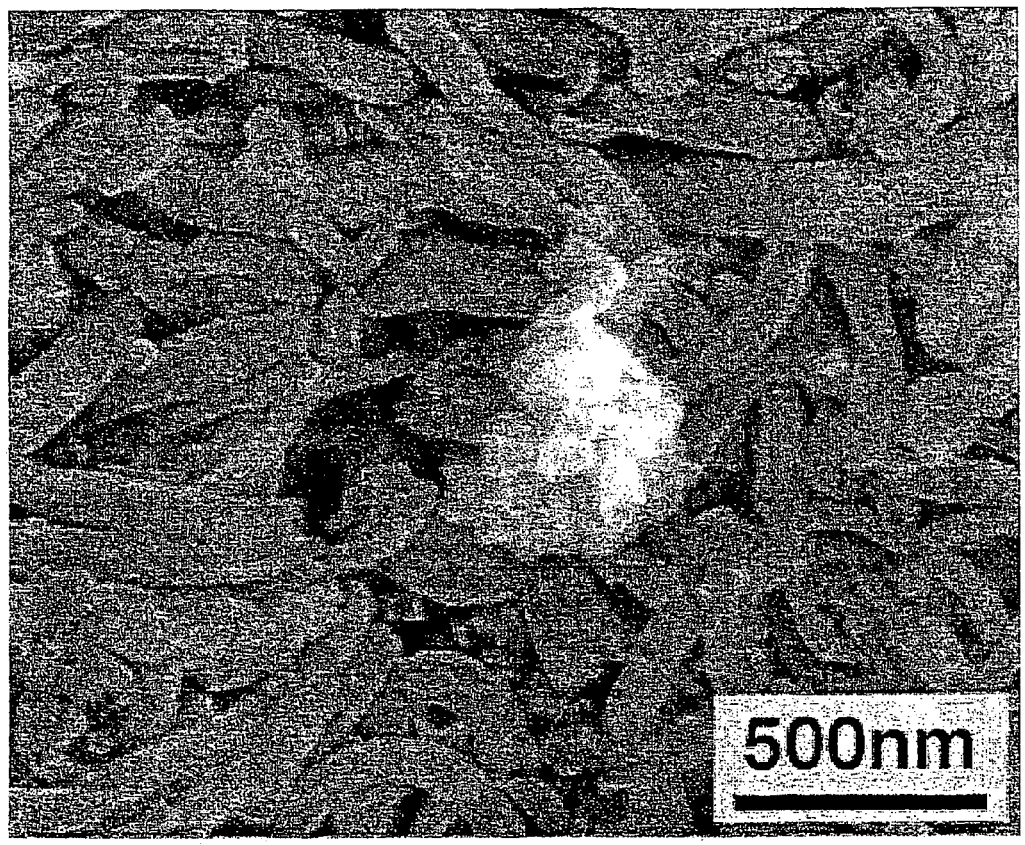
FIG. 4 is an SEM photograph of an aggregate surface in Example 6.

The multilayer carbon nanotube aggregate obtained in Example 6 was confirmed by SEM, TEM and the X ray photoelectron spectrometry. An SEM photograph of the aggregate surface is shown in FIG. 4. From FIG. 4, it is found that the aggregate is formed from the multilayer carbon nanotubes alone.

Figure 5:
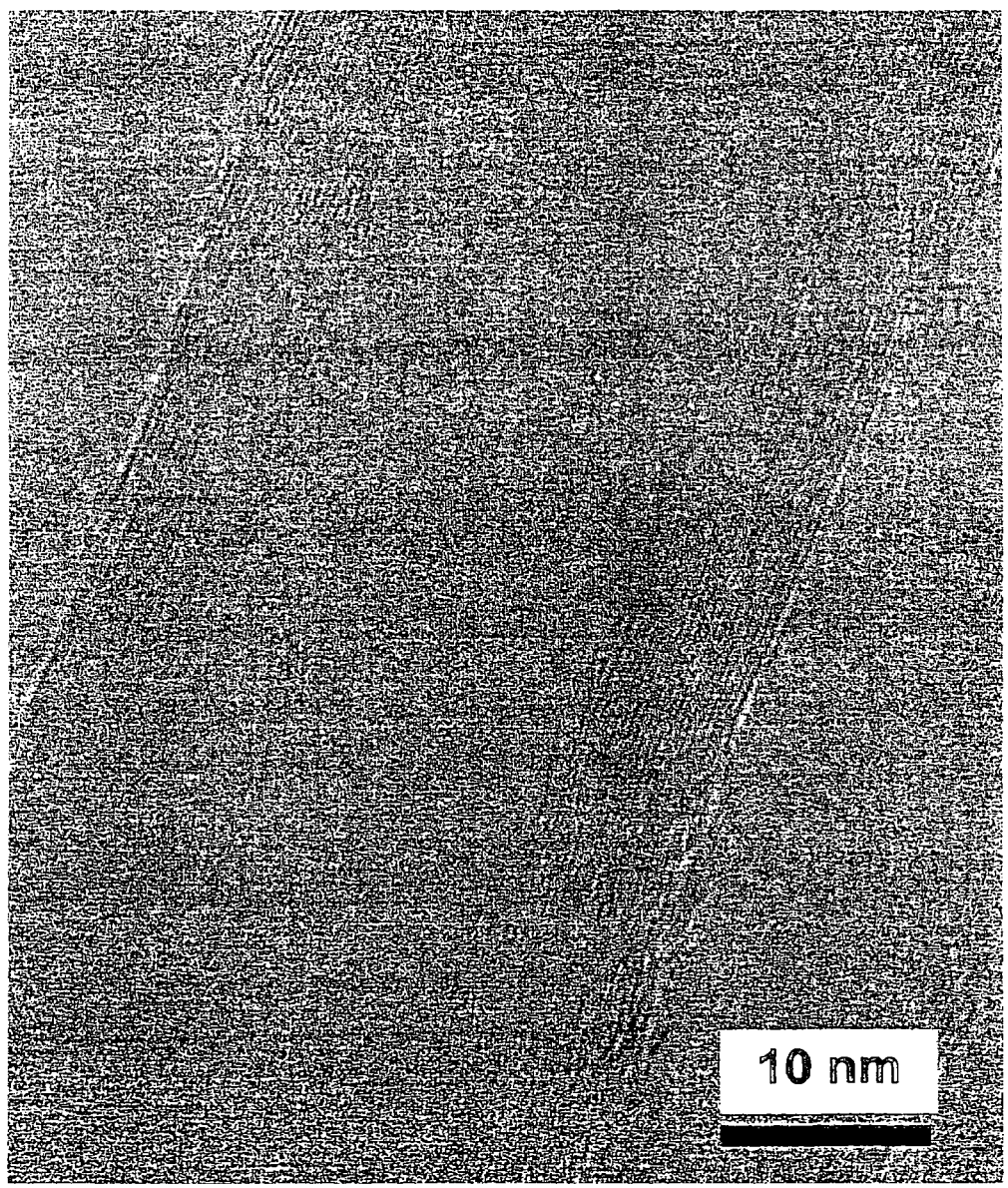
FIG. 5 is a TEM photograph of the aggregate in Example 6.

A TEM photograph of the aggregate is shown in FIG. 5. In FIG. 5, the expansion of the interlayer intervals of the outer layers identified in FIG. 2 was not identified. This indicates that fluorine has been desorbed from the multilayer carbon nanotubes.

When the C—F bond in the aggregate was analyzed by the X ray photoelectron spectrometry, the peak at C 1s289.5 eV (the charge was compensated by making unmodified carbon 285.0 eV) identified in the fluorinated multilayer carbon nanotubes disappeared. This also indicates that fluorine has been desorbed from the multilayer carbon nanotubes.

Figure 6:
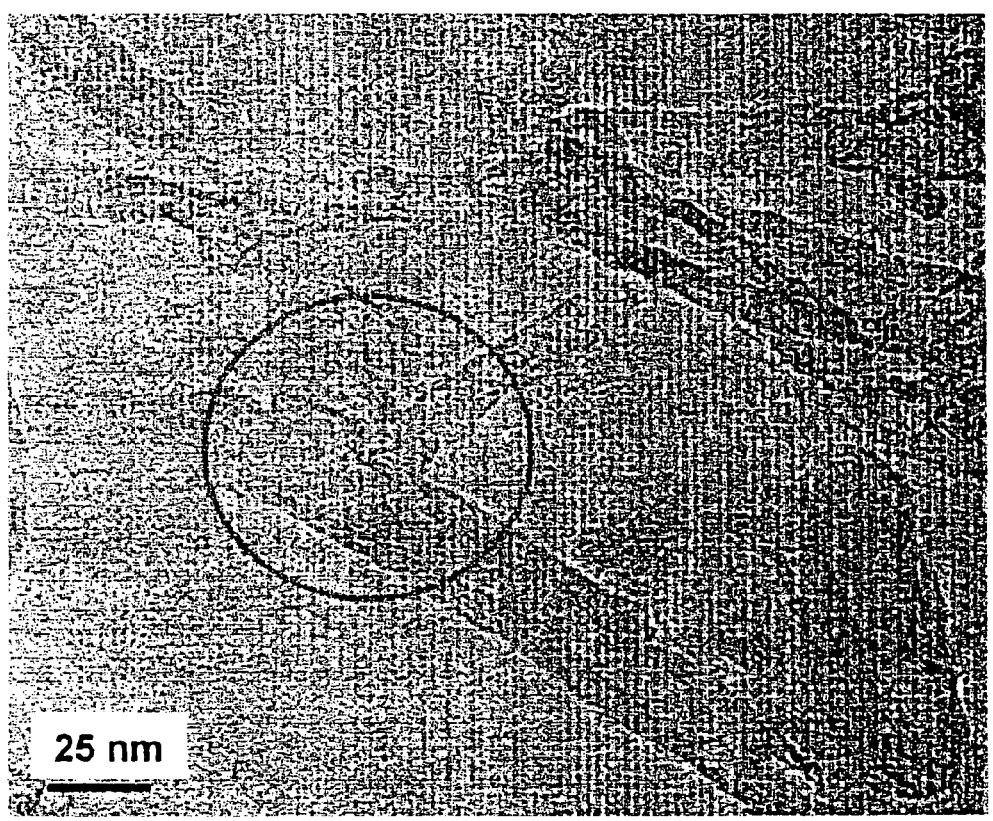
FIG. 6 is a TEM photograph of the aggregate in Example 6.

A TEM photograph of the aggregate is shown in FIG. 6. From FIG. 6, it can be identified that the bond between the tubes has been formed.

Comparative Example 1

Production of Aggregate (8)

The unpurified multilayer carbon nanotube is dried in vacuum at 200° C. for 12 hours. This sample (1 g) is filled in the sintered die with an internal diameter Φ 20 mm and a height of 60 mm made from graphite. The sintered die is set in the SPS apparatus, compressed at 80 MPa and then deaeration inside the chamber is performed. The temperature was raised up to 1000° C. at 25° C./minute and the constant temperature treatment was performed for 10 minutes. After cooling, no multilayer carbon nanotube aggregate was obtained.

Comparative Example 2

Production of Aggregate (9)

The purified multilayer carbon nanotube obtained in Example 1 is dried in vacuum at 200° C. for 12 hours. This sample (1 g) is filled in the sintered die with an internal diameter φ 20 mm and a height of 60 mm made from graphite. The sintered die is set in the SPS apparatus, compressed at 80 MPa and then deaeration inside the chamber is performed. The temperature was raised up to 1000° C. at 25° C./minute and the constant temperature treatment was performed for 10 minutes. After cooling, no multilayer carbon nanotube aggregate was obtained.

Comparative Example 3

Production of Aggregate (10)

The multilayer carbon nanotube in which the defect has been introduced obtained in Example 9 is dried in vacuum at 200° C. for 12 hours. This sample (1 g) is filled in the sintered die with an internal diameter Φ 20 mm and a height of 60 mm made from graphite. The sintered die is set in the SPS apparatus, compressed at 80 MPa and then deaeration inside the chamber is performed. The temperature was raised up to 1000° C. at 25° C./minute and the constant temperature treatment was performed for 10 minutes. After cooling, a multilayer carbon nanotube aggregate was obtained. The resulting aggregate could be processed.

Comparative Example 4

A resol type phenol resin (1 g) is dissolved in ethyl alcohol, and the purified multilayer carbon nanotubes (1 g) obtained in Example 1 are added thereto. Ultrasound is irradiated thereto, which is then sufficiently stirred, and then ethyl alcohol is evaporated to yield phenol resin coated carbon nanotube. The phenol resin is degraded to make an amorphous carbon-added carbon nanotube raw material by heating this at 200° C. in nitrogen and keeping this temperature for 2 hours. This sample (1.3 g) is filled in the sintered die with an internal diameter Φ 20 mm and a height of 60 mm made from graphite. The sintered die is set in the SPS apparatus, compressed at 80 MPa and then deaeration inside the chamber is performed. The temperature was raised up to 1000° C. at 25° C./minute and the constant temperature treatment was performed for 10 minutes. After cooling, a resin-added multilayer carbon nanotube aggregate was obtained. The resulting aggregate could be processed.

Test Example 1

A test piece with a length of 1 mm, a width of 20 mm and a height of 1 mm is made from the multilayer carbon nanotube aggregate (sintered body) obtained in Examples 5 to 7, Examples 10 and 11, and Comparative Examples 3 and 4. The surface of the resulting test piece was smoothened by polishing paper #1200, and then polish powder produced by the previous polishing was removed by wrapping tape #2000. Furthermore, finish was performed using wrapping tape #4000. The sample surface after the polishing was observed using an optical microscope, and for the test piece with no fine scar, the 3-point bending test was performed to measure the mechanical strength (flexural strength, Young's modulus). Three samples were prepared, and their mean was calculated.

A mass of the test piece was measured by an electronic balance (GR-202 supplied from A & D) and a dimension was measured by a slide caliper and a micrometer to calculate a bulk density. Five samples were prepared, and their mean was calculated.

These results are shown in Table 2.

TABLE 2

| Sintered body | Flexural strength (MPa) | Young's modulus (GPa) | Density (g/cm$^3$) |
| --- | --- | --- | --- |
| Example 5 | 98.3 | 15.4 | 1.45 |
| Example 6 | 66.1 | 20.1 | 1.46 |
| Example 7 | 65.8 | 19.9 | 1.44 |
| Example 10 | 76.4 | 12.4 | 1.36 |
| Example 11 | 51.4 | 16.2 | 1.46 |
| Comparative Example 3 | 34.2 | 7.4 | 1.35 |
| Comparative Example 4 | 48.7 | 9.3 | 1.41 |

Test Example 2

A test piece with a length of 1 mm, a width of 5 mm and a height of 1 mm is made from the multilayer carbon nanotube aggregate (sintered body) obtained in Example 6 and Comparative Example 4. The surface of the resulting test piece was smoothened by the polishing paper #1200, and then the polish powder produced by the previous polishing was removed by the wrapping tape #2000. Furthermore, the finish was performed using the wrapping tape #4000. The produced test piece was implanted in a pocket subcutaneously formed in the abdominal area of a Wistar strain male rat with 6 weeks of age under general anesthesia. After one week, the rat was killed and the test piece was removed and fixed together with surrounding tissue. After removing the sample as politely as possible, the sample was embedded with paraffin according to standard methods. Sliced sections were stained with hematoxylin and eosin and searched histologically to determine the affinity. A photograph of the observed tissue surrounding the test piece is shown in FIG. 7.

The results are summarized in Table 3.

TABLE 3

Figure 7:
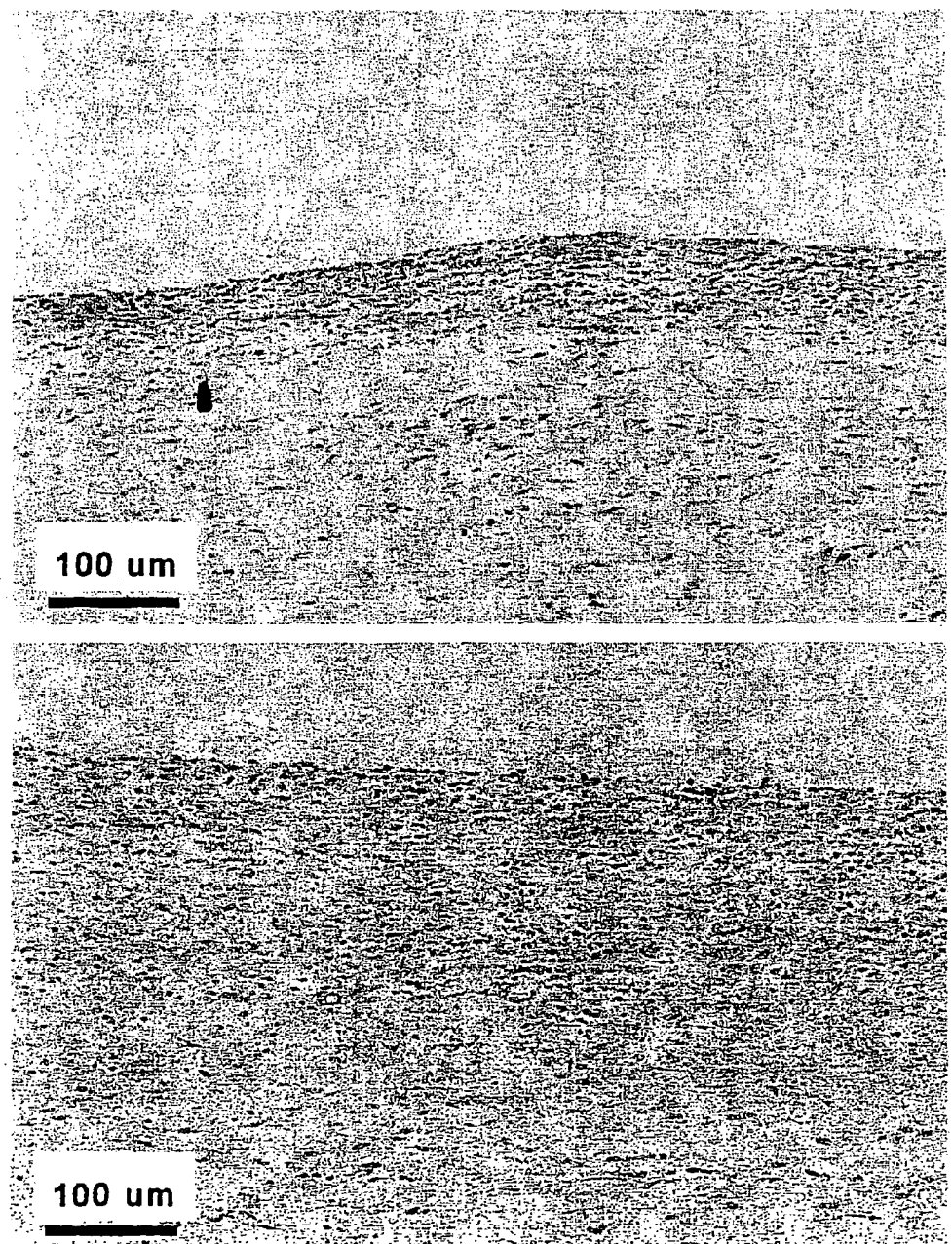
FIG. 7 is observation photographs in Test Example 2 (upper: Example 6, lower: Comparative Example 4).

| Sintered body | Biocompatibility | Comments for FIG. 7 |
| --- | --- | --- |
| Example 6 | Yes | Enfolded with relatively thin fibrous connective tissues including fibroblasts and mesenchymal cells. No inflammatory reaction was identified. |
| Comparative Example 4 | No | Thin fibrous connective tissues including mesenchymal cells, fibroblasts and dilated capillary vessels were observed. Lymphocytes were partially observed to identify the inflammatory reaction. Foreign body giant cells were also observed. |

INDUSTRIAL APPLICABILITY

As described above, the present invention is composed of the step of fluorinating and the step of sintering the fluorinated multiple carbon nanotubes, and enables to form the aggregate of the carbon nanotubes alone. The carbon nanotube aggregate is composed of the carbon nanotubes alone, can be constructed as those combining its properties, and thus, has the possibility to use for various fields.

The invention claimed is:

1. A method for forming a carbon nanotube aggregate, comprising
   (1) modifying multiple carbon nanotubes with fluorine, and
   (2) sintering the multiple carbon nanotubes modified with fluorine.

2. The method for forming a carbon nanotube aggregate according to claim 1, wherein the sintering takes place at a formation temperature of 250° C. to 3000° C. in a non-oxidizing atmosphere.

3. The method for forming a carbon nanotube aggregate according to claim 1, wherein the sintering takes place at a formation pressure of 10 MPa to 600 MPa in a non-oxidizing atmosphere.

4. The method for forming a carbon nanotube aggregate according to claim 1, wherein in step (1) the carbon nanotubes are treated with fluorine ($F_2$) gas in a container made of a fluorine based resin.

5. The method for forming a carbon nanotube aggregate according to claim 4, wherein said fluorine based resin is a perfluorinated fluorine based resin.

6. The method for forming a carbon nanotube aggregate according to claim 1, wherein said carbon nanotube is a monolayer nanotube.

7. The method for forming a carbon nanotube aggregate according to claim 1, wherein said carbon nanotube is a multilayer nanotube.

8. The method for forming a carbon nanotube aggregate according to claim 1, wherein said carbon nanotube is a carbon nanotube in which a defect has been introduced.

9. A carbon nanotube aggregate made by binding multiple carbon nanotubes to one another.

10. A carbon nanotube aggregate formed by the method according to claim 1.

11. A carbon nanotube aggregate made by binding multiple carbon nanotubes to one another, and formed by the method according to claim 1.

12. A biocompatible material comprising the carbon nanotube aggregate according to claim 10.

13. The biocompatible material according to claim 12, wherein the biocompatible material is an artificial joint material, a dental material or an artificial bone material.

14. An electronic material comprising the carbon nanotube aggregate according to claim 10.

15. The electronic material according to claim 14, wherein the electronic material is a biological electrode material, a battery electrode material, a fuel battery electrode material or an electric bilayer capacitor electrode material.

* * * * *